US011561176B2

(12) United States Patent
Schönfuss et al.

(10) Patent No.: US 11,561,176 B2
(45) Date of Patent: Jan. 24, 2023

(54) METHOD FOR DEGRADATION-COMPENSATED EVALUATION OF LUMINESCENCE SENSOR DETECTION SIGNALS, AND EVALUATION APPARATUS THEREFOR

(71) Applicant: Hamilton Bonaduz AG, Bonaduz (CH)

(72) Inventors: Dirk Schönfuss, Tamins (CH); Valentin Verschinin, Chur (CH)

(73) Assignee: HAMILTON BONADUZ AG, Bonaduz (CH)

( * ) Notice: Subject to any disclaimer, the term of this patent is extended or adjusted under 35 U.S.C. 154(b) by 256 days.

(21) Appl. No.: 17/055,871

(22) PCT Filed: May 13, 2019

(86) PCT No.: PCT/EP2019/062235
§ 371 (c)(1),
(2) Date: Nov. 16, 2020

(87) PCT Pub. No.: WO2019/219624
PCT Pub. Date: Nov. 21, 2019

(65) Prior Publication Data
US 2021/0223176 A1    Jul. 22, 2021

(30) Foreign Application Priority Data
May 16, 2018    (DE) .................... 10 2018 207 666.9

(51) Int. Cl.
*G01N 21/64* (2006.01)
*G01N 21/77* (2006.01)
(Continued)

(52) U.S. Cl.
CPC ......... *G01N 21/6408* (2013.01); *G01N 21/77* (2013.01); *G01N 21/85* (2013.01);
(Continued)

(58) Field of Classification Search
CPC .... G01N 21/6408; G01N 21/77; G01N 21/85; G01N 33/497; G01N 2021/6432;
(Continued)

(56) References Cited

U.S. PATENT DOCUMENTS 4,845,368 A * 7/1989 Demas ................. G01T 1/2045
250/328
6,701,168 B1  3/2004 Wilson et al.
(Continued)

FOREIGN PATENT DOCUMENTS

| EP | 2887054 A1 | 6/2015 |
| GB | 2496657 A | 5/2013 |

(Continued)

OTHER PUBLICATIONS

English translation of the Written Opinion of the International Searching Authority issued in International Application No. PCTEP2019062235.

*Primary Examiner* — David P Porta
*Assistant Examiner* — Gisselle M Gutierrez
(74) *Attorney, Agent, or Firm* — Tollefson IP

(57) ABSTRACT

A method is provided for degradation-compensated evaluation of detection signals of a sensor arrangement operating on the principle of luminescence quenching, which arrangement has a luminophore that degrades over time, an excitation radiation source, and at least one optical sensor. The luminophore radiates, in accordance with a response characteristic of the sensor arrangement, in reaction to irradiation with a predefined modulated excitation radiation and as a function of the extent of an interaction of the luminophore with a quencher substance that quenches the luminescence of the luminophore. A response radiation is detected by the at least one optical sensor. The sensor arrangement outputs a detected intensity value representing an intensity of the response radiation and a detected phase value representing a phase difference of the response radiation with respect to the modulation of the excitation radiation. A predetermined (Continued)

calibration value correlation is identified in consideration of the reference response characteristic.

15 Claims, 5 Drawing Sheets

(51) Int. Cl.
    *G01N 21/85*      (2006.01)
    *G01N 33/497*      (2006.01)

(52) U.S. Cl.
    CPC ............... *G01N 33/497* (2013.01); *G01N 2021/6432* (2013.01); *G01N 2021/7763* (2013.01); *G01N 2021/7786* (2013.01); *G01N 2021/8578* (2013.01); *G01N 2201/1211* (2013.01)

(58) Field of Classification Search
    CPC .......... G01N 2021/7763; G01N 2021/7786; G01N 2021/8578; G01N 2201/1211; G01N 2021/7796; G01N 2201/024; G01N 21/645; G01N 2021/6434; G01N 21/274; G01N 21/643
    See application file for complete search history.

(56) References Cited

U.S. PATENT DOCUMENTS

| | | | |
|---|---|---|---|
| 7,926,322 | B1 | 4/2011 | Queen |
| 2002/0158212 | A1* | 10/2002 | French ............... B01L 3/50853 252/301.16 |
| 2003/0023181 | A1 | 1/2003 | Mault |
| 2003/0050543 | A1* | 3/2003 | Hartmann .......... A61B 5/14542 436/172 |
| 2003/0099574 | A1* | 5/2003 | Bentsen ............. G01N 21/6408 422/82.07 |
| 2008/0085217 | A1* | 4/2008 | Mueller ............... G01N 21/643 422/83 |
| 2008/0215254 | A1* | 9/2008 | Leiner .................... C09B 57/08 702/25 |
| 2010/0032583 | A1 | 2/2010 | Kane |
| 2010/0171043 | A1 | 7/2010 | Burke et al. |
| 2018/0356342 | A1* | 12/2018 | Laycock ............... G02B 26/06 |

FOREIGN PATENT DOCUMENTS

| | | |
|---|---|---|
| WO | 2003009763 A1 | 2/2003 |
| WO | 2008148703 A1 | 12/2008 |

* cited by examiner

Normalized phase value

Normalized phase value

METHOD FOR DEGRADATION-COMPENSATED EVALUATION OF LUMINESCENCE SENSOR DETECTION SIGNALS, AND EVALUATION APPARATUS THEREFOR

CROSS-REFERENCE TO RELATED APPLICATIONS

This application is the National Stage of International Application No. PCT/EP2019/062235, filed on May 13, 2019, which claims the benefit of German Application No. 10 2018 207 666.9, filed on May 16, 2018. The entire contents of both applications are hereby incorporated herein by reference.

BACKGROUND OF THE INVENTION

The present invention relates to a method for degradation-compensated evaluation of detection signals of a sensor arrangement operating on the principle of luminescence quenching. The present invention furthermore relates to an evaluation apparatus embodied to carry out such a method.

A sensor arrangement operating according to the principle of luminescence quenching comprises a luminophore, an excitation radiation source, and at least one optical sensor. As a reaction to irradiation with a predefined modulated excitation radiation, the luminophore radiates, in accordance with a response characteristic typical of the sensor arrangement, a response radiation that is detected by the at least one optical sensor. The response radiation depends not only on the excitation radiation of the excitation radiation source, but also on the extent to which the luminophore interacts with a quencher substance. The quencher substance, for instance oxygen, has the property of quenching a luminescence of the luminophore. The luminophore luminescence brought about by the excitation radiation therefore decays more quickly in the presence of the quencher substance that interacts with the luminophore than would be the case in the absence of the quencher substance. The response characteristic in this context is the material-immanent correlation, dependent on the extent of interaction with the quencher substance, between the excitation radiation and the response radiation of the predefined luminophore.

As a rule, such sensor arrangements are used instrumentally not only to detect but to quantify the presence of a specific quencher substance. If, for example, oxygen is a quencher substance for a predefined luminophore, the sensor arrangement can be used to ascertain the oxygen content or oxygen concentration in a test fluid that is to be tested. For this, the test fluid must be brought into luminescence-quenching interaction with the luminophore, for example, in the case of collisional quenching, into physical contact with the luminophore.

The luminescence quenching produced by the quencher substance causes a change, as a function of the concentration of the quencher substance in the test fluid, in a phase angle of a phase shift between the modulated excitation radiation and a response radiation that is thus necessarily also modulated. Using a form of the Stern-Volmer equation (known per se) which takes into account the phase angle between the excitation radiation and response radiation, it is possible to determine, from a phase angle of the response radiation which is identified for a known excitation radiation, a concentration of the quencher substance, for instance in the form of a partial pressure of the quencher substance in the test fluid.

The luminescence quenching produced by the quencher substance causes, for a predefined excitation radiation, a change in an intensity of the response radiation which depends on the concentration of the quencher substance in the test fluid. Using a form of the Stern-Volmer equation which takes into account the intensity of the response radiation, it is again possible to determine, from an intensity of the response radiation which was identified for a known excitation radiation, a concentration of the quencher substance.

Detection signals of the sensor arrangement therefore represent, as a rule, either a phase angle or an intensity of the response radiation.

Based on a calibration of the sensor arrangement carried out before a concrete detection operation, it is possible very generally to associate, with a detection signal that is based on the response radiation detected by the optical sensor, a result value that represents the desired result, for example a concentration of a predetermined quencher substance in a test fluid, for instance the oxygen partial pressure in a test fluid. What is identified in the context of calibration of the sensor arrangement is therefore very generally a calibration value correlation that links values of the detection signal, based on the response radiation, to result values.

The objective of an evaluation of detection signals of a sensor arrangement operating according to the principle of luminescence quenching is to ascertain the result value that is the goal of the detection operation.

It is problematic in this context that a luminophore degrades over time, for instance by so-called "bleaching." Assuming a constant excitation radiation and constant concentration of the quencher substance in the test fluid, the response radiation of the luminophore radiated in reaction to the excitation radiation changes as degradation of the luminophore used in a sensor arrangement progresses. In the terminology used above, this means that the material-immanent response characteristic of the luminophore changes in degradation-related fashion.

In the present Application, a reference to degradation of the luminophore is equivalent to a reference to degradation of the sensor arrangement.

As degradation of the luminophore progresses, the difference between the response characteristic currently existing at the respective detection time, and the reference response characteristic which previously existed during calibration and on which the (still valid) calibration value correlation is based, increases. As a consequence, the result values that are determined based on current detection signals, and on the basis of a calibration at a time in the past, increasingly deviate from the true value, for example (in the case of bleaching, which constitutes a very common form of degradation) toward detection values that are too low. Because the luminescence quenching property of the luminophore means that decreasing detection values are associated with rising quencher-substance concentrations as result values, degradation of the luminophore as a rule leads to the identification of result values that are quantitatively too high.

The calibrated sensor arrangement, when used as intended in order to determine result values on the basis of the respectively valid response characteristic, always supplies some detection value and as a consequence, on the basis of the respectively valid calibration value correlation, some result values from the detection values. For the user of the sensor arrangement, it is not possible in the existing art to recognize whether an identified high result value results from degradation of the luminophore, or from an actually high concentration of the quencher substance.

One approach to avoiding degradation-related errors in the identification of result values is to calibrate the sensor arrangement as frequently as possible, and thus adjust the reference response characteristic that is the basis of the calibration to the current response characteristic that changes as a result of degradation of the luminophore. This quite considerably decreases the productivity of the sensor arrangement, however, because of the time required for calibration.

Another approach is to correct the result values that are incorrect due to degradation. A proposal for doing so is known from EP 2 887 054 A1.

The teaching of this document is to take into account in correcting fashion a degradation of the luminophore in the Stern-Volmer equation used for evaluation of the sensor arrangement detection signal, the Stern-Volmer equation being used in a form that uses the detected phase angle as an argument.

EP 2 887 054 A1 proposes to modify both the baseline phase value of the Stern-Volmer equation, i.e. the phase angle that is identified in the absence of the quencher substance using a new, undegraded luminophore, and the Stern-Volmer constant used in the equation, by means of respective aging factors. The aging factors are in turn dependent on the modulation frequency of the excitation radiation. They must be empirically ascertained very laboriously for each sensor type (because of their dependence on the sensor structure), and for several modulation frequencies of the excitation radiation (because of their frequency dependence).

The Stern-Volmer equations used in accordance with EP 2 887 054 A1 are degradation-corrected using exponential functions, different exponential functions, constituting correction factors, being multiplied by the baseline phase value and by the Stern-Volmer constant. The respective aging factors are part of the exponents of the exponential functions. Because of the equation structure resulting therefrom, degradation correction according to EP 2 887 054 A1 requires laboriously numerically solving an equation system for each detection operation, which either requires provision of an evaluation apparatus having unusually high computation performance or, in a context of conventional computation performance, delays the detection operation until the desired result value has been obtained. The degradation correction proposed in EP 2 887 054 A1 is furthermore dependent on the operating duration of the sensor, which in reality is not necessarily the case.

SUMMARY OF THE INVENTION

The object of the present invention is therefore to furnish a technical teaching which makes it possible to eliminate to the greatest extent possible, with less complexity than heretofore and with greater accuracy to the extent possible, the influence of luminophore degradation on the evaluation of detection signals of a sensor arrangement operating according to the principle of luminescence quenching.

This object is achieved, in accordance with the present invention, by a method for degradation-compensated evaluation of detection signals of a sensor arrangement operating on the principle of luminescence quenching, which arrangement comprises a luminophore that degrades over time, an excitation radiation source, and at least one optical sensor. The luminophore radiates, in accordance with a response characteristic typical of the sensor arrangement, in reaction to irradiation with a predefined modulated excitation radiation and as a function of the extent of an interaction of the luminophore with a quencher substance that quenches the luminescence of the luminophore, a response radiation detected by the at least one optical sensor. The sensor arrangement outputs, as detection signals, a detected intensity value representing an intensity of the response radiation and a detected phase value representing a phase difference of the response radiation with respect to the modulation of the excitation radiation. For an accomplished detection of a response radiation, a quantitative deviation of one of the detected values, from among a detected intensity value and detected phase value, is quantitatively decreased in accordance both with the detected intensity value and with the detected phase value, the deviation being based on a degradation-based change in the response characteristic at the time the detection was accomplished with respect to a reference response characteristic whose basis is a calibration of the sensor arrangement. A degradation-compensated detected value is thus identified. A result value of the accomplished detection, referred to the quencher substance, is then determined on the basis of the degradation-compensated detected value in accordance with a predetermined calibration value correlation identified in consideration of the reference response characteristic.

Unlike in EP 2 887 054 A1, the evaluation method of the present invention, highly advantageously, does not utilize either the detected phase value or the detected intensity value in order to compensate for luminophore degradation, but instead utilizes for that purpose both values obtainable in the context of a detection (phase value and intensity value). This is because it has been discovered, entirely surprisingly, that for a given sensor arrangement operating according to the principle of luminescence quenching, the intensity value and the phase value are respectively uniquely correlated in each degradation state. The intensity value, represented as a function of the phase value, maps as a constant, sufficient, and unique graph. The same applies, of course, to the phase value as a function of the intensity value. For a predefined excitation radiation and for different concentrations of quencher substance in a test fluid, a sufficient and unique correlation between the phase value and the intensity value of a response radiation is therefore associated with a given sensor arrangement.

Also surprisingly, this applies regardless of whether the concentration of the quencher substance in a test fluid to be tested using the sensor arrangement or, for example, the temperature of the test fluid and/or of the sensor arrangement, changes. For a sensor arrangement calibrated on the basis of a reference response characteristic existing at the time of calibration (preferably a brand-new sensor arrangement), an intensity value can always be uniquely associated with a phase value, and vice versa, for each concentration of the quencher substance in the test fluid and for each temperature of the test fluid. A change in the concentration of the quencher substance and/or a change in the temperature of the test fluid causes the detection values that are then obtained in a detection operation only to shift along the correlation, but not to depart from it. This correlation between phase value and intensity value for different concentrations of quencher substance in the test fluid, and if applicable for different test fluid temperatures, will be referred to hereinafter simply as a "correlation" or "phase value/intensity value correlation."

This unique correlation between the phase value and intensity value for a predefined response radiation and for a test fluid having different concentrations of quencher substance is an example of a response characteristic of the sensor arrangement or of a sensor arrangement type that is identical in terms of design and luminophore. Because of the uniqueness of the correlation, it is immaterial whether the intensity value is regarded as a function of the phase value, or the phase value as a function of the intensity value. As will become apparent below with reference to the exemplifying embodiment, it can be more practical to use as a baseline detection value that detection value which is the input variable for utilization of the calibration value correlation for calculation of the result value, and to construe or use the respective other detection value as a function of the baseline detection value.

As was stated above, when considering only one of the detection signals or values that are obtained, i.e. either only the phase value or only the intensity value, it is impossible to ascertain whether that value is correct or that value is distorted, since the current response characteristic of the sensor arrangement differs, due to degradation of the luminophore, from the reference response characteristic on which the calibration value correlation, still being used, of the sensor arrangement is based. In accordance with the present invention, conversely, simultaneous consideration both of the phase value and of the intensity values makes it very possible to ascertain whether, for example, the detection is based on a degraded luminophore or on a luminophore that corresponds to the calibration being used.

As was the case previously, one of the two detected values, from among the phase value and intensity value, is sufficient for identification of the result value. Both values are needed, however, in order to ascertain whether the response characteristic of the luminophore of the sensor arrangement corresponds sufficiently to the reference response characteristic that is the basis for the calibration being used, or has changed in the meantime due to degradation of the luminophore. If the value pair of phase value and intensity value lies outside a predefined tolerance range, selectable in principle without restriction but within reason, around the known correlation between the phase value and intensity value of the sensor arrangement in its state at the most recent calibration (calibration state), the luminophore has degraded beyond the tolerance threshold that is the basis of the predefined tolerance range. Expressed in graphical terms, the detection-value pair made up of the phase value and intensity value lies, in a two-dimensional Cartesian coordinate system whose axes represent respectively the phase value and the intensity value, away from the constant curve that represents the correlation between phase value and intensity value in the calibration state of the sensor arrangement for different concentrations of quencher substance in the test fluid. The "calibration state" here is the state of the sensor arrangement at the point in time of the most recent calibration, i.e. the one currently still being used.

Also entirely surprisingly, it has been found that the correlation between the phase value and intensity value of a sensor arrangement is unique and sufficient even in a degradation state deviating from the calibration state, and simply differs from the phase value/intensity value correlation of the calibration state. Considered graphically, the respective detection-value pair of phase value and intensity value of a sensor arrangement for different concentrations of the quencher substance in the test fluid and/or for different temperatures of the test fluid respectively lie, in a Cartesian coordinate system having the aforesaid axes for the calibration state and for each degradation state, on a unique constant curve and/or can be described by a respectively unique equation, the individual curves of the various degradation states exhibiting shapes or profiles that are similar to one another but are shifted and/or tilted with respect to one another.

If the respective correlations of phase values and intensity value, for a predefined sensor arrangement or a predefined type of sensor arrangement, are known for different degradation states, it is possible to ascertain the degradation state (if applicable, utilizing extrapolation or interpolation) from a value pair of phase value and intensity value obtained during a detection, and to identify from that state the corresponding theoretical value pair of phase value and intensity value that would have been outputted as detection signals (detection-value pair) under otherwise identical detection conditions in the calibration state. Instead of a value pair, only one value from among the phase value and intensity value of that theoretical value pair can be outputted. That value (phase value or intensity value) of the theoretical value pair is consequently a degradation-compensated value based on which the actually desired result value can be identified using the calibration value correlation that is already present.

The correlations of intensity value and phase value for different concentrations of the quencher substance in the test fluid and/or for different temperatures of the test fluid, in different degradation states from brand-new or undegraded to completely degraded, can be ascertained empirically on one or more sensor arrangements of a given sensor arrangement type, and then stored in a data memory of an evaluation apparatus for that type of sensor arrangement. In principle, a single calibration of the sensor arrangement, for instance when it is first put into service, can then suffice, since later detection results in degradation states can be referred back to the calibration state by way of the known empirically identified correlations, optionally with the aid of extrapolation or interpolation. After such an identification of the degradation-compensated detected value, a sufficiently correct result value can be identified based on the calibration value correlation currently being used.

Proceeding from the empirically identified value pair correlations, in order to facilitate identification of the degradation-compensated detected value it is possible to develop, from the value pair correlations, a function system or equation system that facilitates computational identification of the degradation-compensated detected value. For example, isoconcentration correlations or functions or traces or profiles, which proceed over several intensity value/phase value correlations of the calibration state and of the individual degradation states and connect, for a predefined temperature of the test fluid, those value pairs of intensity value and phase value which are respectively associated with the same concentrations of the quencher substance for different degradation states of the sensor arrangement type, can be determined. These can be determined experimentally for concentrations of the quencher substance in steps at a predetermined step interval, for example every 10 percentage points for a concentration indicated as a volume percentage or weight percentage. These functions can likewise be stored in a data memory of an evaluation apparatus. Intermediate values of concentration values, for which no functions were ascertained, are calculated by extrapolation or interpolation.

A function family or equation family of this kind can in turn be identified for several relevant test-fluid temperatures, so that a degradation-compensated detected value can also be correctly calculated from detection signals for detection operations at different test-fluid temperatures. Detection signals from detection operations that were obtained at test-fluid temperatures deviating from those test-fluid temperatures can be processed by extrapolation or interpolation.

Such function systems or equation systems, or function system families or equation system families, constitute very generally a compensation value correlation that links detected intensity and phase values to a degradation-compensated detected value. That compensation value correlation can exist graphically as curves or curve families, analytically as an equation system or equation system family, or in table form, and can be stored in a data memory. Analytical representations of the compensation value correlation can be obtained by fitting equations (in a manner known per se) to point families obtained by experimental measurements and/or from theoretical considerations, for example in the course of a method of least error squares.

A compensation value correlation can also be furnished by only a single function or curve or table, as will be shown below.

According to a refinement of the present invention, the method according to the present invention therefore encompasses the step of identifying the degradation-compensated detected value on the basis of a predetermined compensation value correlation with input variables on the basis of the detected intensity value and the detected phase value. Because one detected value is sufficient for identification of the result value, preferably only exactly one detected value, from among a detected intensity value and detected phase value, is preferably degradation-compensated on the basis of a predetermined compensation value correlation on the basis of both the detected intensity value and the detected phase value.

The method above can, however, be simplified in extremely advantageous fashion by the fact that the above-described correlations between phase value and intensity value for different concentrations of quencher substance in a test fluid, and thus the response characteristic, in the context of a predefined excitation radiation are considered not in a dimension-affected space but rather in a dimensionless space, and used at least for part of the evaluation. The reason is that it has been shown that the functions of the correlations of phase value and intensity value always form the same dimensionless phase value/intensity value correlation for a given sensor arrangement type in the calibration state. In the dimension-affected space it is always possible to ensure by calibration, for sensor arrangements of a given sensor arrangement type, that the response characteristic of a sensor arrangement for a detection operation corresponds to the reference response characteristic. The individual reference response characteristics associated with the different degradation states differ from one another depending on the degradation state of the sensor arrangement.

Entirely surprisingly, it has been found that regardless of the physical degradation state of a sensor arrangement, in dimensionless notation its reference response characteristics are always the same. Degradation of the luminophore since the most recent calibration causes the current response characteristic to become increasingly different, even in dimensionless notation, from the reference response characteristic that was the basis for creation of the calibration value correlation that is still being used. In dimensionless notation, however, recalibration of the sensor arrangement does not result in a new dimensionless reference response characteristic (as would be the case in a dimension-affected notation), but instead leads back to the already known dimensionless reference response characteristic. This enormously simplifies the outlay in terms of computation performance and computation infrastructure required for degradation compensation.

Because of this situation it is possible, particularly advantageously, for a single equation or function to be sufficient as a compensation value correlation for identifying the degradation-compensated detection value.

This effect is based, in terms of physical calculation theory, on the fact that degradation of the luminophore causes a change in its performance, but not in the technical processes and effects that are the basis of that performance. The differences that depend on the degradation state can be, as it were, "short-circuited" if both the detected intensity value and the detected phase value are transformed, utilizing at least one system parameter characterizing the sensor arrangement and/or at least one process parameter deriving from the detection process, respectively into a dimensionless detected intensity value and into a dimensionless detected phase value. Such a transformation is not obligatorily necessary in order to achieve the advantages of the present invention, but the advantages can be achieved more quickly, with less outlay in terms of computer infrastructure, and with higher accuracy in a dimensionless notation for the detection operations.

In terms of similarity theory, transitioning the consideration and data-related processing of a technical operation from a dimension-affected to a dimensionless notation signifies a transition from a standards system external to the noted process, for example the system of SI units, to a process-inherent system of coordinates or standards. This is known, for instance, from flow mechanics: for example, flows having the same value for the dimensionless Reynolds number behave entirely identically in terms of specific flow-mechanical effects regardless of the medium that is flowing, the specific flow rate, and the dimensions of the flow. In a dimension-affected notation, for instance in the SI system, those flows would be described by the same basic equations but with completely different parameter values. In a system-inherent dimensionless notation, they are all described by the same quantitatively identical value.

This is similarly the case here for the sensor arrangements of the same type, in which context calculation of far less complicated dimensionless variables is sufficient. For example, each detected phase value can be converted into a dimensionless phase value by being divided by a reference phase value that is predetermined and quantified by experiment. The predetermined and quantified reference phase value can be, for example, the phase value yielded by the sensor arrangement for a predetermined quencher concentration in the test fluid, for instance for a quencher proportion of 50 vol % or 50 wt %, or for a predetermined quencher partial pressure. The same is correspondingly true, mutatis mutandis, for transformation of the detected intensity value, the reference phase value and the reference intensity value preferably being determined at the same quencher concentration.

For better comparability and thus for easier data-related processing of the detected values (phase value and intensity value), the latter are preferably transformed into a dimensionless normalized detected intensity value and a dimensionless normalized detected phase value. This can be achieved by the fact that firstly a predetermined extreme value, for instance the detection value for a maximum concentration of the quencher substance, i.e. when pure quencher substance is used as a test fluid, is subtracted from the respective detected value. For sensor arrangements operating according to the principle of luminescence quenching, this is usually a quantitatively minimal detection value. The difference amount thereby obtained is then divided by the absolute value of the maximum possible obtainable detection value range of the sensor arrangement or of the sensor arrangement type. This range again is a difference amount, and is identified by calculating the difference between the, as a rule quantitatively maximum, detection value for a minimum concentration of the quencher substance, i.e. when using the test fluid completely devoid of quencher substance, and the detection value for a maximum concentration of the quencher substance. These latter difference amounts, which describe the respective maximum possible value range of the respective detection value, are then the aforesaid reference phase value for the phase value constituting a detection value, and the reference intensity value for the intensity value constituting a detection value.

The reference phase value and reference intensity value are preferably determined immediately after calibration, in order to ensure that the current response characteristic of the sensor arrangement matches the reference response characteristic that is the basis of the calibration.

In the case of dimensionless normalization of the detection signals, they always have values that are between 0 and 1.

The predetermined compensation value correlation is then preferably a predetermined dimensionless compensation value correlation, so that the dimensionless normalized detection value can be compensated, directly and without prior reconversion back into a dimension-affected value, in terms of a possible degradation of the luminophore. In accordance with the dimensionless compensation value correlation, the degradation-compensated detected value can be identified with input variables on the basis of the dimensionless, preferably normalized, detected intensity value and of the dimensionless, preferably normalized, detected phase value. The degradation-compensated detection value is then preferably also a dimensionless, particularly preferably a dimensionless normalized, degradation-compensated detected value or detection value.

If the degradation-compensated detected value is a dimensionless, preferably a dimensionless normalized, degradation-compensated detected value, it can either be converted into a dimension-affected degradation-compensated detected value and the result value can then be determined, with an input variable on the basis thereof, with the predetermined calibration value correlation. Or the predetermined calibration value correlation is embodied to determine the result value directly, with an input variable on the basis of the dimensionless, preferably dimensionless normalized, degradation-compensated detected value. For this, the predetermined calibration value correlation can be, but need not be, a dimensionless, preferably a dimensionless normalized, predetermined calibration value correlation.

The term "input variable on the basis of a value" includes both the value itself and a functional value of a function whose argument is the value.

Not only are the dimensionless reference response characteristics of a given sensor arrangement or a given sensor arrangement type identical regardless of the degradation state of the sensor arrangement. The dimensionless response characteristics of a given sensor arrangement or a given sensor arrangement type are also identical, for the same degradation state with respect to the calibration state of the currently used calibration value range, over a wide range of the usable operating lifetime of a sensor arrangement. It is therefore possible, with the aid of a dimensionless compensation value correlation, to accomplish a degradation compensation of the detection value without even needing to determine beforehand whether or not the sensor arrangement is degraded. The dimensionless detection-value pair is merely applied to the currently obtained dimensionless detection-value pair. It is sufficient for the dimensionless compensation value correlation to refer a detection value of the detection-value pair back to the known degradation-invariant dimensionless reference response characteristic. The dimensionless compensation value correlation can therefore be a mapping instruction that transfers only one of the two detected values, which both, due to aging or degradation of the luminophore, lie outside the degradation-invariant correlation of a dimensionless intensity value and dimensionless phase value which represents the reference response characteristic, onto the known degradation-invariant phase value/intensity value correlation on the basis of the two detected values.

In principle, the degradation-compensated detected value can be either a degradation-compensated detected phase value or a degradation-compensated detected intensity value. Because previous experience indicates that the phase value producible by modulation of the excitation radiation yields the result value having the higher accuracy upon evaluation, the degradation-compensated detected value is preferably the degradation-compensated detected phase value. This applies regardless of the notation of the detected value in a dimension-affected, dimensionless, or normalized value space.

The aforesaid object is furthermore achieved by way of an evaluation apparatus that is embodied to execute the method described above. The evaluation apparatus is thus embodied for degradation-compensated evaluation of detection signals of a sensor arrangement that operates according to the principle of luminescence quenching and has a luminophore that degrades over time, has an excitation radiation source, and has at least one optical sensor; the luminophore radiating, in accordance with a response characteristic typical of the sensor arrangement, in reaction to irradiation with a predefined modulated excitation radiation and as a function of the extent of an interaction of the luminophore with a quencher substance that quenches the luminescence of the luminophore, a response radiation detected by the at least one optical sensor; the evaluation apparatus comprising a data input channel that is embodied to transfer from the sensor arrangement to a data processing unit of the evaluation apparatus, as detection signals, a detected intensity value representing the intensity of the response radiation and a detected phase value representing the phase difference of the response radiation with respect to the modulation of the excitation radiation; the data processing unit comprising a data memory for storing data and a computation unit for processing data; at least the predetermined calibration value correlation identified in consideration of the reference response characteristic being stored in the data memory; the evaluation apparatus being embodied to ascertain the degradation-compensated detected value from the detected intensity value and detected phase value in accordance with both the detected intensity value and the detected phase value, and to determine and output the result value, referred to the quencher substance, of the accomplished detection in accordance with the calibration value correlation on the basis of the degradation-compensated detected value.

The computation unit can be realized by way of a microcomputer, an integrated circuit, and the like. The evaluation apparatus can be a computer having a data processing program which is executable thereon and is stored in a data memory that is data-transferringly connected to the computation unit. The above advantageous refinements of the method are also refinements of the evaluation apparatus for carrying out the method.

In accordance with the statements made regarding the method according to the present invention, the evaluation apparatus can additionally or alternatively be embodied to identify, from a comparison between a pair of detection signals associated with a detection operation and the reference response characteristic which is stored in the data memory and on which the currently used calibration value correlation is based, whether the luminophore of the sensor arrangement is degraded beyond a predefined tolerance threshold. This is the case whenever the pair of detection signals in the coordinate plane that is defined by the phase value and intensity value is located outside a predefined tolerance band around the phase value/intensity value correlation which represents the reference response characteristic. The tolerance threshold can be zero but preferably differs quantitatively from zero, since the phase value/intensity value correlation is a correlation interpolated between individual anchor points, and offers only an approximate correlation in the interpolation region itself. The evaluation apparatus preferably outputs a warning message if it identifies a degradation of the luminophore which extends beyond the predetermined tolerance threshold. Identification of a degradation that is no longer within tolerances can be based on the processing of dimension-affected and/or dimensionless and/or normalized values as data.

According to a preferred refinement of the evaluation apparatus, the predetermined compensation value correlation is also stored in the data memory. The computation unit is preferably embodied to identify the degradation-compensated detected value in accordance with the predetermined compensation value correlation with input values on the basis of the detected intensity value and of the detected phase value.

According an even further preferred refinement, the evaluation apparatus can be embodied to transform both the detected intensity value and the detected phase value, utilizing at least one system parameter characterizing the sensor arrangement and/or at least one process parameter deriving from the detection process, into a dimensionless detected intensity value, preferably into a dimensionless normalized detected intensity value, and into a dimensionless detected phase value, preferably into a dimensionless normalized detected phase value; the predetermined compensation value correlation being a predetermined dimensionless compensation value correlation in accordance with which, with input variables on the basis of the dimensionless detected intensity value and the dimensionless detected phase value, the preferably dimensionless, particularly preferably dimensionless normalized, degradation-compensated detected value is identified.

Correspondingly to the above description of the method, the degradation-compensated detected value can be a dimensionless, preferably a dimensionless normalized, degradation-compensated detected value, and the predetermined calibration value correlation can be a dimensionless, preferably a dimensionless normalized, predetermined calibration value correlation. The evaluation apparatus is then preferably embodied to ascertain the result value in accordance with the preferably dimensionless calibration value correlation with an input variable on the basis of the dimensionless degradation-compensated value. Alternatively, the evaluation apparatus can be embodied to convert a dimensionless, preferably a dimensionless normalized, degradation-compensated value into a dimension-affected degradation-compensated value, and to calculate the result value on that basis using the calibration value correlation.

The aforementioned object is also achieved by a measurement arrangement encompassing an evaluation apparatus embodied as described above, as well as a sensor arrangement having a luminophore that degrades over time, having an excitation radiation source, and having at least one optical sensor; the luminophore radiating, in accordance with a response characteristic typical of the sensor arrangement, in reaction to irradiation with a predefined modulated excitation radiation and as a function of the extent of a contact of the luminophore with a quencher substance that quenches the luminescence of the luminophore, a response radiation detected by the at least one optical sensor.

BRIEF DESCRIPTION OF THE DRAWING FIGURES

The present invention will be explained in further detail below with reference to the appended drawings, in which.

Figure 6:
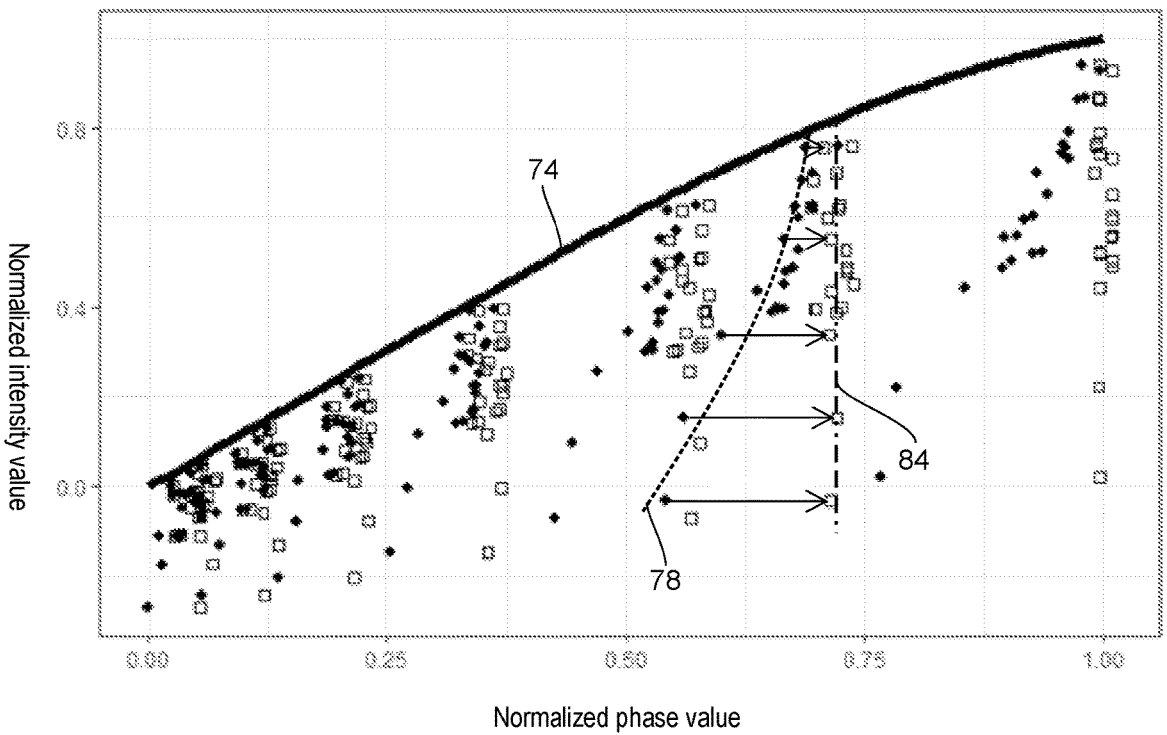
FIG. 6 shows the plot of FIG. 5 with hypothetical phase values that are associated with the detection-value pairs and would have been obtained with a non-degraded sensor arrangement.
Figure 7:
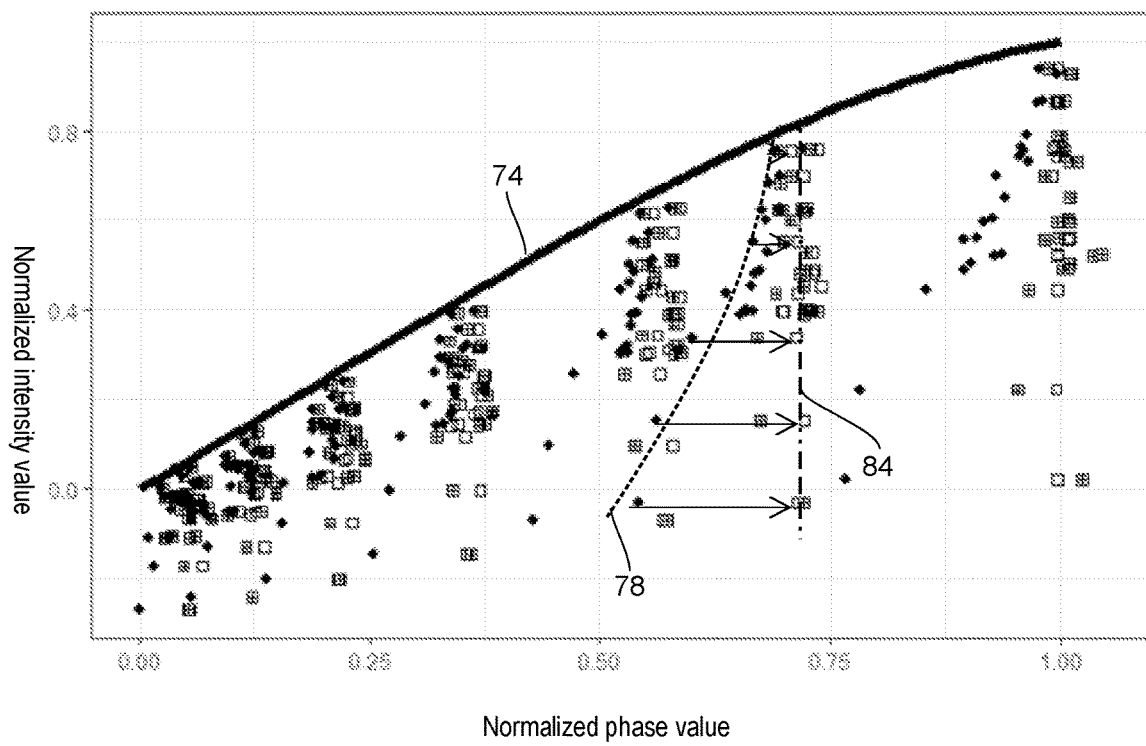
Figure 8:
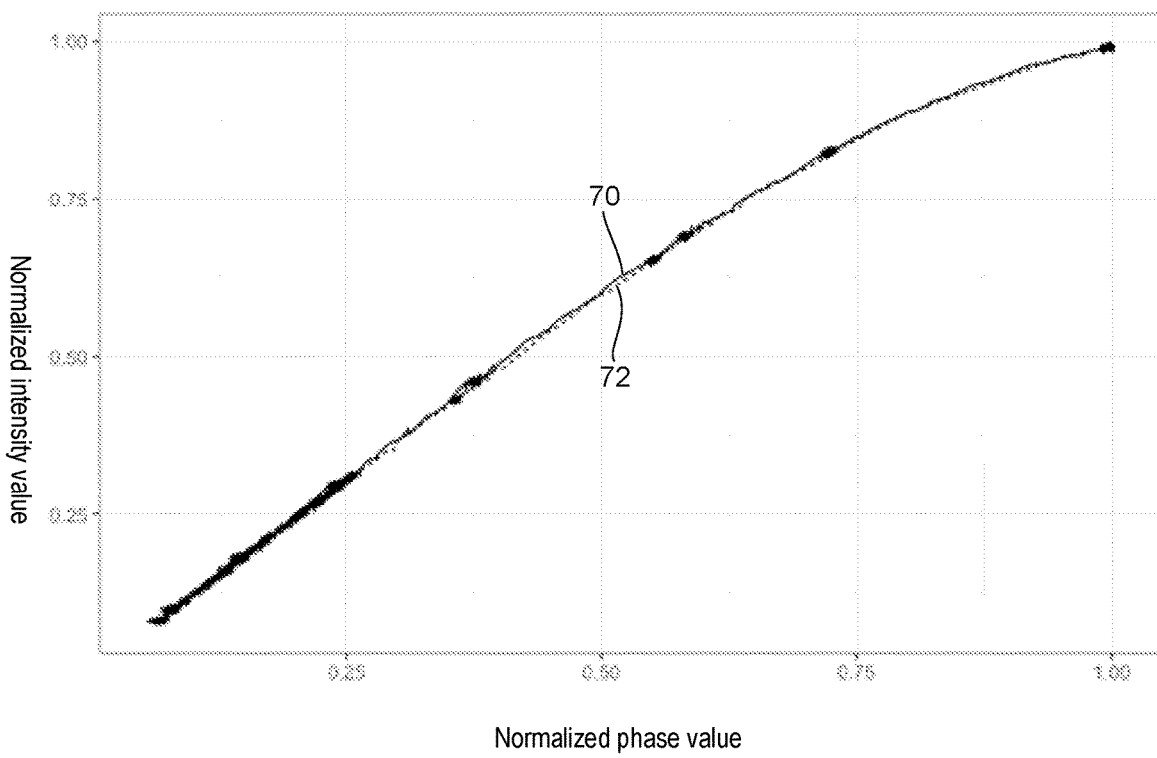

FIG. 7 shows the plot of FIG. 6 with compensated phase values, additionally associated with the detection-value pairs, which were obtained based on a compensation function equation constituting a compensation value correlation; and FIG. 8 shows normalized dimensionless plots of a freshly calibrated sensor arrangement in the brand-new state, and of a freshly calibrated sensor arrangement having a degraded luminophore.

DETAILED DESCRIPTION OF THE PREFERRED EMBODIMENTS

Figure 1:
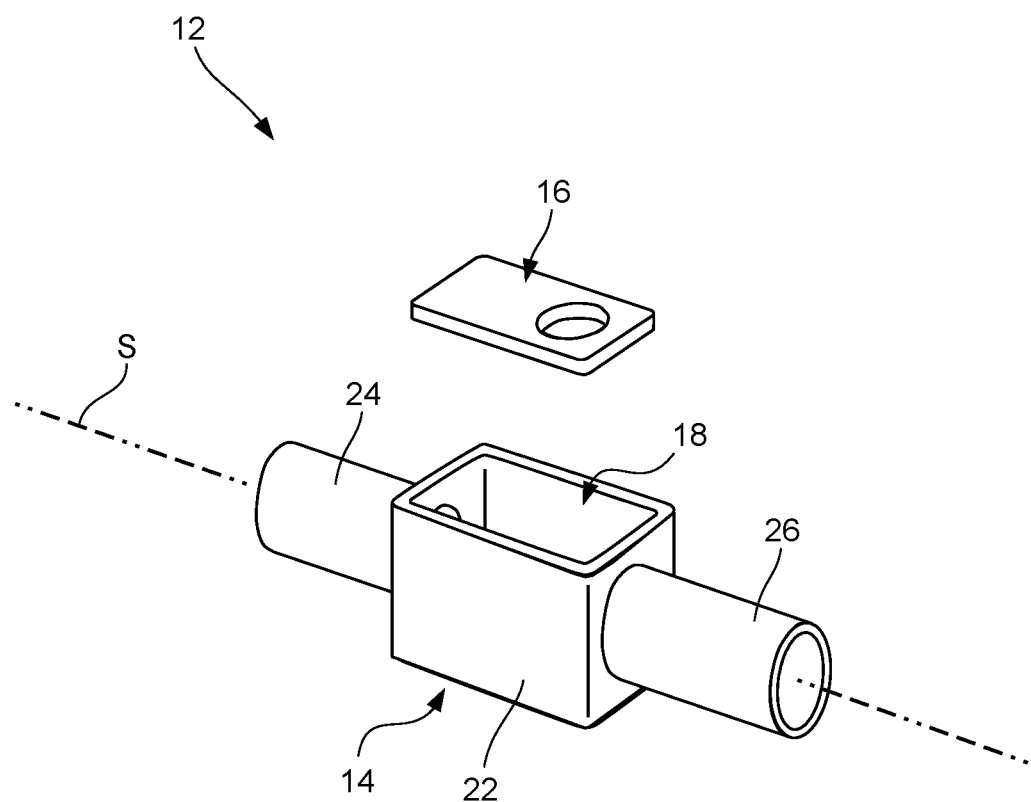
FIG. 1 is a partial exploded view of a housing of a sensor arrangement operating according to the principle of luminescence quenching.

FIG. 1 is a partly exploded view depicting a housing 12 of a sensor arrangement operating according to the principle of luminescence quenching.

Housing 12 encompasses a base housing 14 and a window component 16 having a luminophore-containing layered component arrangement 20 (see FIG. 2) that is arranged therein but is not visible in FIG. 1. An opening 18 in base housing 14 can be closed off with window component 16.

Housing 12 has, on both sides of parallelepipedal portion 22 constituted with the participation of window component 16, connector fittings 24 and 26 for connecting fluid line portions thereto.

Housing 12 is flow-capable bidirectionally along flow axis S.

Figure 2:
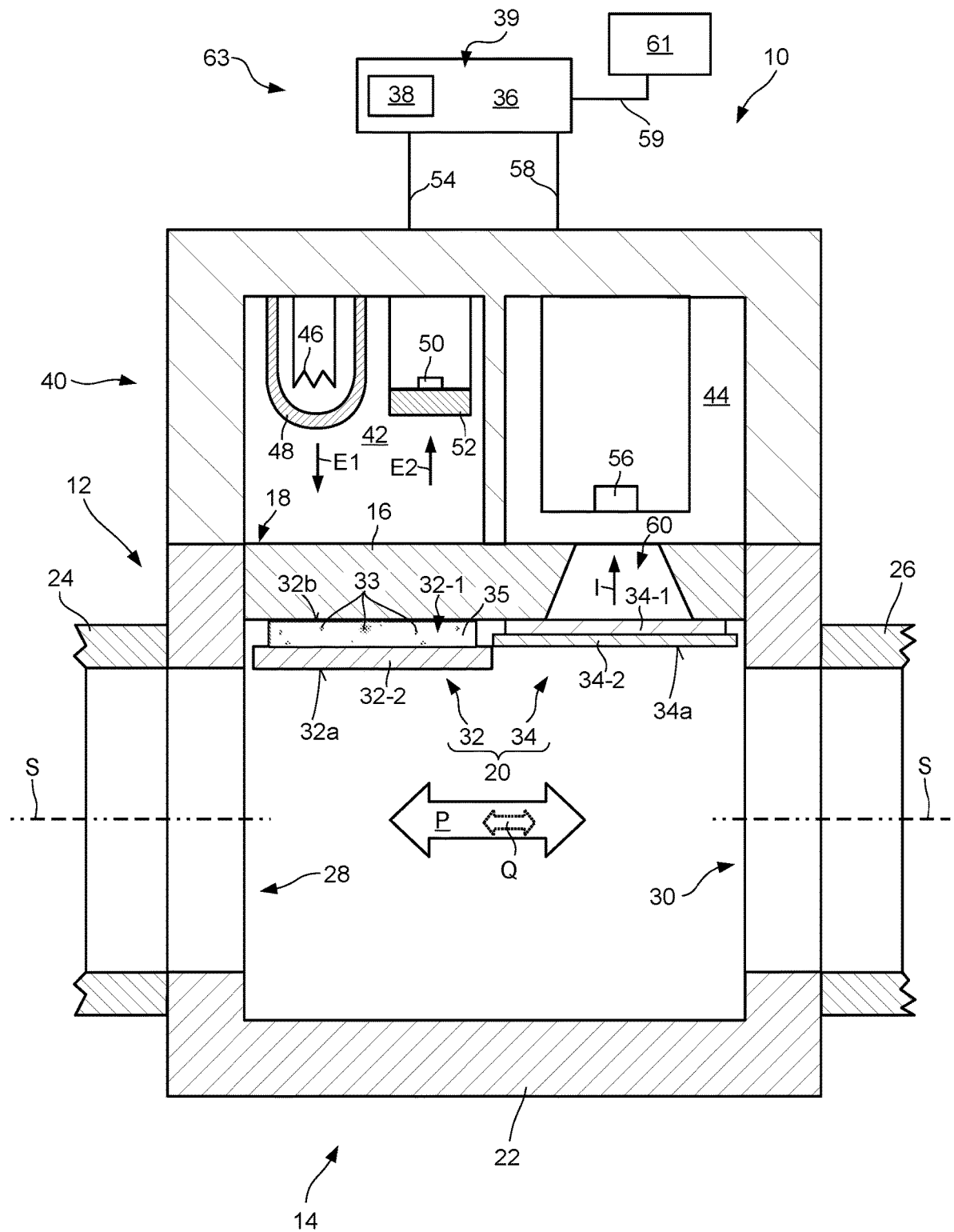
FIG. 2 is a schematic cross section through a sensor arrangement of the present invention.

FIG. 2 is a schematic cross section of the sensor arrangement, labeled in general with the number 10.

Test fluid P can flow bidirectionally along flow axis S through housing 12 between its two openings 28 and 30. Test fluid P flows past fluid contact sides 32a and 34a of layered elements 32 and 34, making contact with them. Flow axis S lies in the drawing plane of FIG. 2.

In the example depicted, sensor arrangement 10 is embodied for temperature-compensated luminophore-based detection of the oxygen partial pressure of a test fluid P, here e.g. air, flowing through housing 12. Oxygen thus constitutes in the present case an example of quencher substance Q recited in general above. The test fluid can be or can encompass a gas or a liquid. The test fluid can be a two-phase substance having both a liquid and a gas. The test fluid can be a suspension of liquid and solid particles, an emulsion, and a similar mixture. Sensor arrangement 10 can be configured, for example, to ascertain the oxygen content in inspiratory and/or expiratory respiratory gas that is delivered to and carried away from a patient by means of a ventilation apparatus.

In the present example, sensor arrangement 10 is embodied for temperature compensation. It is thereby possible to convert detection signals that were obtained from a test fluid P having a temperature that deviates from the calibration temperature of a fluid, used for calibration, having a known concentration of quencher substance Q, into detection signals that would have been obtained if test fluid P had exhibited the calibration temperature in the detection operation. The present invention also functions, however, on sensor arrangements that are not embodied for temperature compensation.

Both temperature compensation and conversion of the directly obtained detection values into an oxygen concentration or oxygen content of test fluid P are accomplished by a control device 36 on the basis of calibration information stored in a data memory 38 of control device 36. In the present case the calibration information encompasses also, but not only, the aforementioned calibration value correlation. Control device or computation device 36, and data memory 38, together constitute a data processing unit 39.

A sensor subassembly 40, which preferably can be arranged detachably on housing 12 and for that purpose, for example, surrounds parallelepipedal portion 22 on three sides in a U-shape, the base of the "U" being located opposite window component 16, encompasses (in the exemplifying embodiment depicted) two measurement chambers 42 and 44 that are physically separated from one another.

Provided in measurement chamber 42, which serves to identify the oxygen concentration as a desired result value, is an excitation radiation source 46, for example in the form of an LED, which emits an electromagnetic excitation radiation E1 having a first wavelength. In order for the wavelength band of electromagnetic excitation radiation E1 that proceeds from excitation radiation source 46 to be kept as narrow as possible, and to avoid interference radiation, excitation radiation source 46 can be surrounded by a filter element 48 that allows the electromagnetic excitation radiation E1 of the recited wavelength to pass with the smallest possible wavelength tolerance.

Reaction layer 32-1 of layered element 32 contains a luminophore 33 that is retained in a matrix 35 and can be excited by excitation radiation E1 to luminesce.

Also arranged in first measurement chamber 42 is a radiation detector 50 that detects an electromagnetic response radiation E2 that proceeds from reaction layer 32-1 after the latter is excited by electromagnetic excitation radiation E1. Radiation detector 50 can also be preceded by a radiation filter 52 in order to allow the passage only of electromagnetic response radiation E2 having its second wavelength that differs from the wavelength of excitation radiation E1. With filter arrangements 48 and 52 it is possible to ensure that no radiation travels directly from excitation radiation source 46 to radiation detector 50, creating "noise" in the signal detected there.

The signal outputted by radiation detector 50 as a result of its detection of response radiation E2 is transferred via data line 54 (shown in FIG. 1) to control device 36. It represents, in a manner known per se, the oxygen partial pressure and thus the result value for test fluid P flowing through housing 12.

Arranged in second measurement chamber 44, which is optionally present and serves for temperature compensation of the detection signal of radiation detector 50, is an infrared detector 56 that detects infrared radiation I radiated from detection layer 34-1. The signal outputted by infrared detector 56 as a result of its detection of infrared radiation I is transferred via data line 58 to control device 36. This signal is indicative of a temperature of detection layer 34-1 and, because of the high thermal conductivity of layered element 34, also indicative of the temperature of the luminophore-containing reaction layer 32-1 that interacts thermally with the same flow of test fluid.

Based on the calibration information stored in data memory 38 of control device 36, which was identified in a separate calibration operation before productive utilization of sensor arrangement 10, control device 36 can identify the temperature of reaction layer 32-1, from the detection signal of infrared detector 56, for each time at which a signal of radiation detector 50 is detected, and can thereby compensate the detection signal of radiation detector 50 with respect to the temperature of the radiating layered reaction element 32 or reaction layer 32-1 thereof. The result is a highly accurate determination of the oxygen partial pressure in test fluid P that is flowing through housing 12.

The highly accurate temperature compensation is achieved with extremely simple means, for example a metal foil constituting carrier layer 34-2, and detection layer 34-1 carried thereon. Detection layer 34-1 preferably encompasses or is a carbon-containing paint containing carbon as a black color pigment. The carbon-containing paint therefore has a very high emissivity of more than 0.9. Utilization of the metal foil as carrier layer 34-1, embodied by way of example from an aluminum foil in the interest of optimum thermal conduction and having a thickness preferably of no more than 12 µm, makes it possible to embody, in window component 16 or in general in housing 12, a hole 60 that passes through window component 16 or through housing 12 and is completely covered by layered element 34. The temperature information radiated, as infrared radiation I, from detection layer 34-1 thus reaches infrared detector 56 with as little distortion as possible.

Measurement chamber 44, having infrared detector 56, detection layered element 34, and hole 60, is omitted in the case of a sensor arrangement 10 not embodied for temperature compensation.

So much for the indirect identification of the temperature of reaction layer 32-1 and consideration thereof in the identification of the result value from the detection signals obtained from radiation detector 50. Now back to the evaluation of the detection signals of radiation detector 50.

Optical, luminophore-based detection of an oxygen concentration, for instance in the form of the oxygen partial pressure, in a test fluid P, is known. In the present exemplifying embodiment it is accomplished with the participation of layered reaction element 32. In the present case, layered reaction element 32 has two plies. In actuality, layered reaction element 32 can have only one layer or also more than two layers. In the example depicted, as is apparent from the cross-sectional view of FIG. 2, layered reaction element 32 comprises a carrier ply 32-2 and luminophore-containing reaction layer 32-1 carried thereon.

The ratios of the length and width of layered reaction element 32 to its thickness are not to scale in the Figures. Layered reaction element 32 that is depicted can have an edge length from approximately 7 to 10 mm, and its thickness, measured over the two layers 32-1 and 32-2, can be approximately 300 µm.

Carrier ply 32-2 can be constituted from a material that is sufficiently porous for oxygen molecules, for example polyvinylidene fluoride. Carrier ply 32-2 can be cut out from a corresponding film and can have a thickness of between 100 and 150 µm. In some circumstance the thickness of carrier ply 32-2 can also be less.

Luminophore-containing reaction layer 32-1 can likewise contain polyvinylidene fluoride as a matrix material into which luminophores are embedded.

Luminophore-containing reaction layer 32-1 can be embodied to be somewhat smaller than carrier ply 32-2 that carries it, in order to facilitate adhesive attachment of layered reaction element 32 with the detection side on window component 16 or in general on housing 12, without thereby needing to apply adhesive to detection side 32b of luminophore-containing reaction layer 32-1.

The depiction of temperature-detection layered element 34 is also not to scale in terms of its dimensions. In the example depicted, it has an edge length in the same range as layered reaction element 32, but because of its structure which differs from layered reaction element 32, as a rule it is thinner than the latter.

Detection sides 32b and 34b, facing toward detectors 50 and 56, of the two layered elements 32 and 34 are advantageously directed outward, i.e. away from test fluid P, while the respective fluid contact sides 32a and 34a of the two layered elements come into contact with the fluid over the largest possible area.

In order to ensure that only oxygen dissolved in test fluid P reaches reaction layer 32-1, the layered reaction element is covered on its detection side 32b by window component 16. Window component 16 can be constituted from a transparent polyamide or also from another plastic that is transparent to the excitation radiation and response radiation. Window component 16 can be constituted, for example, from amorphous polyamide, such as that offered under the name "Grilamid TR" by EMS-Chemie AG in Domat (Switzerland).

Figure 3:
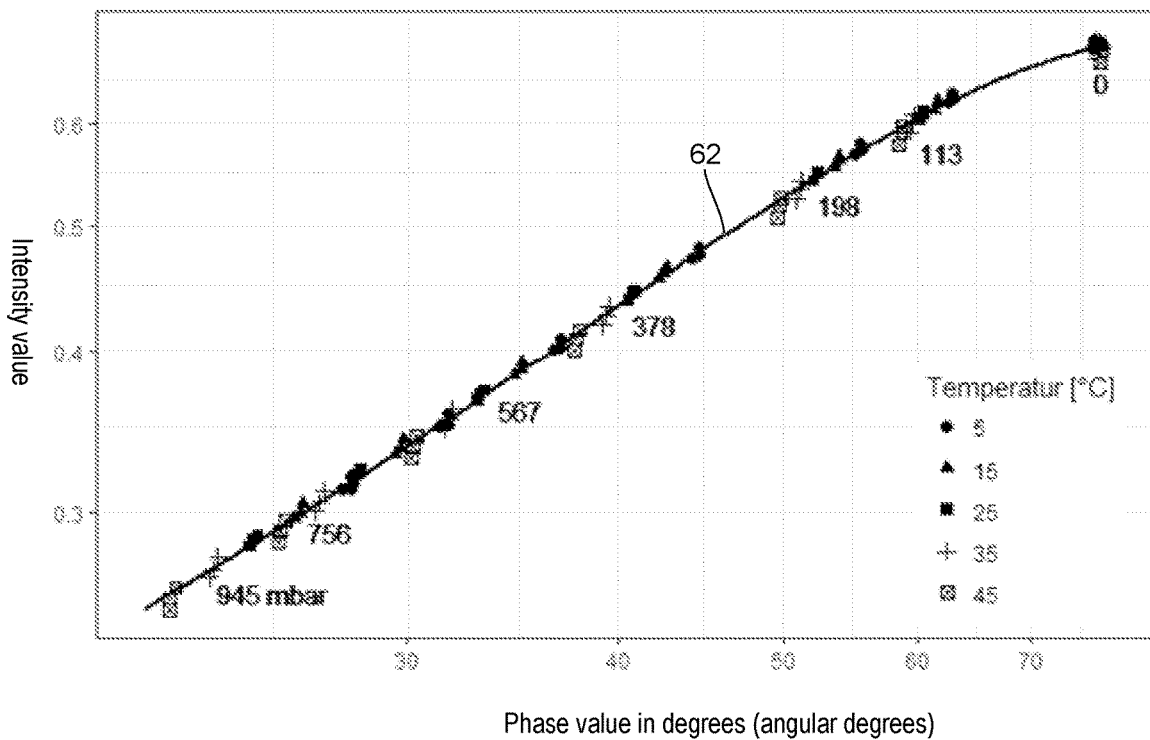
FIG. 3 shows a plot of an intensity of a response radiation of the sensor arrangement of FIG. 2 as a function of the phase shift or phase angle.

FIG. 3 depicts a graph of a functional correlation between a phase value (in degrees) plotted on the abscissa and an intensity value plotted on the ordinate. The graph is labeled with the reference character 62.

During the operation of sensor arrangement 10, excitation source 46 emits excitation radiation E1 having a predetermined intensity modulation.

Response radiation E2 emitted by luminophore-containing reaction layer 32-1 in response to the modulated excitation radiation E1 therefore also exhibits a modulated intensity. Two detection values of sensor arrangement 10 are thus obtainable from response radiation E2: an intensity value representing the intensity of response radiation E2, and a phase value indicating the phase offset between the two modulated radiations. The intensity value can be outputted, for example, as a ratio of the intensity of response radiation E2 to the intensity of the excitation radiation E1.

Because, as described above, an interaction with a quencher substance Q, in the present case e.g. oxygen, in test fluid P quenches the luminescence of the luminophore in reaction layer 32-1 depending on the quantity of quencher substance Q present in test fluid P, and thus influences both the intensity value and the phase value of response radiation E2, it is possible to infer the concentration of quencher substance Q in test fluid P from each individual one of the two detection values (intensity value and phase value) by means of a calibration value correlation.

For a phase value $\phi$, for example, a calibration value correlation can be indicated by the calibrated Stern-Volmer equation indicated below:

$$\frac{\tan(\phi)}{\tan(\phi_0(T))} = \frac{m_2}{1 + K_{sv}(T)p_{O_2}} + \frac{1 - m_2}{1 + m_1 K_{sv}(T)p_{O_2}} \quad \text{(Eq. 1)}$$

where the detected phase value $\phi$ is an exemplifying detection value, $\phi_0(T)$ is the previously known or experimentally identified temperature-dependent phase value in the complete absence of quencher substance Q, $K_{sv}(T)$ is a previously known or experimentally identified temperature-dependent Stern-Volmer coefficient, $p_{O_2}$ is the oxygen partial pressure constituting an exemplifying result value, and $m_1$ and $m_2$ are calibration constants identified in the calibration operation.

Equation 1, constituting an exemplifying calibration value correlation, is solvable numerically or analytically, once the phase value $\phi$ is detected, for the oxygen partial pressure $p_{O_2}$ constituting the result value. The oxygen partial pressure can thus be ascertained directly from the detected phase value.

One of the two possible detection values is therefore sufficient for identification of the oxygen partial pressure as an exemplifying result value that represents a concentration of quencher substance Q in test fluid P.

The luminophore contained in reaction layer 32-1 of sensor arrangement 10 of FIG. 2 always outputs a response radiation E2 in response to an excitation radiation E1. The material-immanent response characteristic that determines the luminescence behavior of the luminophore in response to excitation radiation E1 changes, however, as a result of aging, for example bleaching, of the luminophore.

A different response radiation E2, and thus different detection values (intensity value and phase value), are thus respectively obtained for a given excitation radiation E1 and for a given concentration of quencher substance Q using a given sensor arrangement 10, depending on the degradation state of sensor arrangement 10.

The result of the degradation of the luminophore is that the possible detection values (intensity value and phase value) change, based on a calibration state whose basis is a reference response characteristic of the luminophore existing at the time of calibration, toward lower values for both intensity and phase angle (phase value).

A technician working with sensor arrangement 10 who obtains, for example, only a phase value as a detection value based on a detection operation for a test fluid, can be certain only within a sufficient time span since the most recent calibration operation, in which span the calibration value correlation still being used was identified, that he or she, using the calibration value correlation, can infer the correct result value from the detection value that was obtained.

If, however, a risk exists that the luminophore has been degraded as a result of aging since the most recent calibration, without further actions it cannot be determined whether a low detection value that is obtained is produced by an actually higher concentration of quencher substance Q in test fluid P, or whether age-related degradation of the luminophore is responsible for the low value. On the basis of the detection value that is too low as a result of degradation, too high a result value is ascertained for a predefined calibration value correlation.

As the inventor of the present Application has discovered, however, there is a unique functional correlation between the detection values (intensity value and phase value) obtained for a predetermined concentration of quencher substance Q in test fluid P. Graph 62 shows this functional correlation graphically. Surprisingly, this functional correlation continues to exist even when the temperature of test fluid P changes. For graph 62, detection operations using different partial pressures of quencher substance Q in test fluid P were carried out at temperatures from 5 to 45° C., at 10K intervals. In each case, a test fluid P having a known concentration of quencher substance Q was used, namely having a partial pressure, measured in millibars, having the values 0, 113, 189, 378, 567, 756, and 945. The detection-value pairs obtained by way of the exemplifying measurements, which were all obtained for the same response characteristic of the luminophore or of luminophore-containing reaction layer 32-1, can be represented analytically in an equation of suitable structure using, for example, the method of least error squares.

Figure 4:
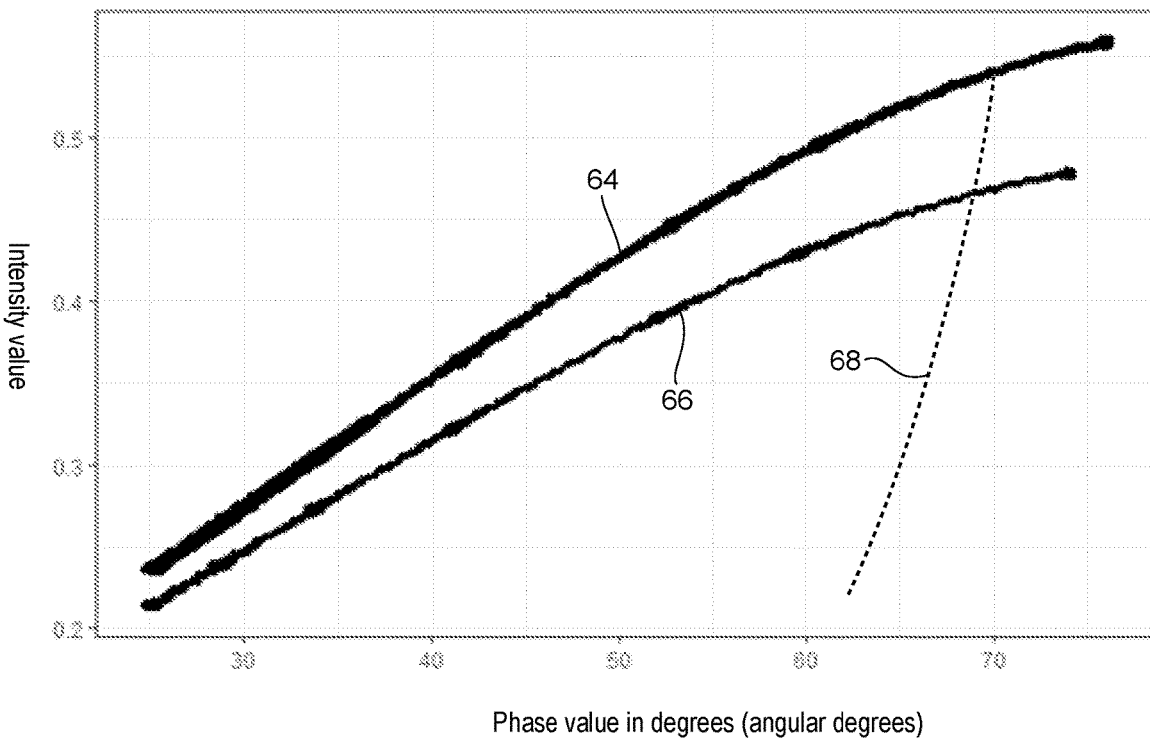
FIG. 4 shows a plot of the intensity of a response radiation as a function of the phase angle, for a freshly calibrated sensor arrangement and for a sensor arrangement that has degraded since it was calibrated.

FIG. 4 shows qualitatively, with reference character 64, a correlation between intensity value and phase value for a brand-new sensor arrangement 10. The depiction corresponds qualitatively to graph 62 of FIG. 3. Compared therewith, graph 66 in FIG. 4 shows a phase value/intensity value correlation of the same sensor arrangement but with an aged luminophore. A comparison of the respective right ends of graphs 64 and 66 in FIG. 4, which show the detection values (intensity value and phase value) for a test fluid from which quencher substance Q is completely absent, illustrates how, with age-related degradation of the luminophore in sensor arrangement 10 and for the same excitation radiation E1, both the intensity value and the phase value of response radiation E2 provoked by excitation radiation E1 decrease.

Thanks to the unique correlation between intensity value and phase value, however, it is possible to ascertain immediately whether a detection value was obtained with a degraded luminophore or with a non-degraded luminophore, the degradation referring in each case to the most recent calibration state for which the freshly calibrated sensor arrangement 10 was functioning perfectly. Graphs 64 and 66 in FIG. 4 are therefore representative of the respective response characteristics of the luminophore in sensor arrangement 10 in the calibration state (see 64) and in a degradation state deviating therefrom (see 66).

When the brand-new sensor arrangement 10 is calibrated, for example, phase value/intensity value correlation 64 represents the reference response characteristic. Sensor arrangement 10 can be utilized for detections of concentrations of quencher substance Q in test fluid P as long as the response characteristic of the luminophore does not change with respect to reference response characteristic 64.

If, however, the response characteristic has developed, for example, toward graph 66 as degradation progresses, sensor arrangement 10 supplies detection values for the respective concentration of quencher substance Q in test fluid P which are too low, and thus ultimately yields incorrect result values. If sensor arrangement 10 is recalibrated in that degradation state, however, the phase value/intensity value correlation represented by graph 66 becomes the reference response characteristic, and sensor arrangement 10 once again yields correct result values. Sensor arrangement 10 will continue to degrade, however, so that incorrect detection values will again be obtained at some time after the most recent calibration.

By considering not just one detection value but both detection values (intensity value and phase value), however, it is possible to identify immediately whether the operating state of the sensor arrangement corresponds sufficiently to the calibration state, or whether it has moved so far away from it, beyond a tolerance threshold, that another calibration is necessary. Calibration operations are unproductive and therefore expensive. The objective is therefore to reduce as much as possible the frequency of calibration of sensor arrangement 10.

A trace 68 drawn with dashed lines in FIG. 4 indicates qualitatively how the phase value and intensity value change, for a test fluid P having a predefined constant concentration of quencher substance Q, as degradation of the luminophore in sensor arrangement 10 progresses. By repeated calibration, the respectively obtained detection value on trace 68 can be linked, in any desired degradation state, with the correct result value, namely the previously known constant concentration of quencher substance Q.

FIG. 8 shows, in this context, an astonishing correlation. If the two graphs 64 and 66 of different degradation states are normalized in such a way that they can contain detection values only between the respective extreme quantitative values of 0 and 1, the normalized dimensionless curves 70 and 72 are respectively obtained for graphs 64 and 66 of FIG. 4. In the normalized dimensionless notation, the two curves are identical.

Normalization can be accomplished, for example for the detected phase value $\phi$ and detected intensity value I, in accordance with Equations 2 and 3 presented below:

$$\phi_N = \frac{\phi - \phi_{min}}{\phi_{max} - \phi_{min}} \qquad (Eq.\ 2)$$

$$I_N = \frac{I - I_{min}}{I_{max} - I_{min}} \qquad (Eq.\ 3)$$

where $\phi_N$ is the normalized dimensionless phase value and $I_N$ is the normalized dimensionless intensity value. The index max denotes the respective quantitatively largest possible detection value, for instance in the complete absence of quencher substance Q, and the index min denotes the respective quantitatively lowest possible detection value, for instance when pure quencher substance Q is used as test fluid P.

The extreme values $\phi_{max}$, $\phi_{min}$, $I_{max}$, and $I_{min}$ used for normalization can be determined either experimentally, or analytically using the approximation calculation shown below by way of example.

For example, the normalized phase value/intensity value correlation of FIG. 8 for a new sensor arrangement 10 of that sensor arrangement type can be described by the following polynomial:

$$_aI_N(\phi_N) = \alpha\phi_N + \beta\phi_N^2 + (1-\alpha-\beta)\phi_N^3 \qquad (Eq.\ 4)$$

having the boundary conditions $_aI_N(0)=0$ and $_aI_N(1)=1$.

Usual fitting methods yield the values α=1.17954 and β=0.26311 for α and β. Equation 4 thus describes a response characteristic of sensor arrangement 10, or of the sensor arrangement type of sensor arrangement 10. It is preferably stored in data memory 38.

The extreme values $\phi_{max}$ and $\phi_{min}$ can be calculated directly, immediately during or after calibration, from Equation 1, where $p_{o_2}=0$ (for $\phi_{max}$) and $p_{o_2}=p_{o_{2,max}}$ (for $\phi_{min}$).

For the dimension-affected value pairs $(\phi_i, I_i)$ used for calibration, the normalized dimensionless phase values $\phi_{N,i}$ can then be calculated using the known $\phi_{max}$, $\phi_{min}$ from Equation 2. Because, from Equations 3 and 4, it must be the case that $$_aI_{N,i} = \frac{_aI_N(\phi_{N,i}) - I_{min}}{I_{max} - I_{min}}, \quad (Eq. 5)$$

the extreme values $I_{max}$ and $I_{min}$ can be identified by, if applicable, numerical solution of the following equation system:

$$I_{max} = \frac{I_2(1 + (\beta(\phi_{N,1} - 1)\phi_{N,1}^2 - \phi_{N,1}^3 + \alpha\phi_{N,1}(\phi_{N,1}^2 - 1)) + I_1(\phi_{N,2}^3 + \alpha\phi_{N,2}(1 - \phi_{N,2}^2) - 1 - \beta(\phi_{N,2} - 1)\phi_{N,2}^2)}{-\phi_{N,1}^3 + \phi_{N,2}^3 + \alpha(-\phi_{N,1} + \phi_{N,1}^3 + \phi_{N,2} - \phi_{N,2}^3) + \beta(-\phi_{N,1}^2 + \phi_{N,1}^3 + \phi_{N,2}^2 - \phi_{N,2}^3)} \quad (Eq. 6)$$

$$I_{min} = \frac{I_2\phi_{N,1}((\beta(\phi_{N,1} - 1) - \phi_{N,1})\phi_{N,1} + \alpha(\phi_{N,1}^2 - 1)) + I_1\phi_{N,2}(\alpha(1 - \phi_{N,2}^2) + \phi_{N,2}(\beta + (1 - \beta)\phi_{N,2}))}{-\phi_{N,1}^3 + \phi_{N,2}^3 + \alpha(-\phi_{N,1} + \phi_{N,1}^3 + \phi_{N,2} - \phi_{N,2}^3) + \beta(-\phi_{N,1}^2 + \phi_{N,1}^3 + \phi_{N,2}^2 - \phi_{N,2}^3)} \quad (Eq. 7)$$

The extreme values need to be determined only upon calibration, however. It is sufficient in this context to use only two values pairs, where i=1, 2.

By way of the extreme values $\phi_{max}$, $\phi_{min}$, $I_{max}$, and $I_{min}$ thereby determined quantitatively, it is possible to identify from Equations 2 and 3, directly and immediately and without great effort, from the dimension-affected detection values $\phi_j$, $I_j$ that are obtained for each detection operation of sensor arrangement 10 or of a sensor arrangement of the same sensor arrangement type, the associated dimensionless normalized detection values $\phi_{N,j}$, $I_{N,j}$.

By comparing the normalized detection values $\phi_{N,j}$, $I_{N,j}$ thereby identified with the values $_aI_{N,j}(\phi_{N,j})$ obtained from Equation 4, it is possible to determine immediately whether or not the luminophore of sensor arrangement 10 is degraded. If such a determination indicates that the luminophore is degraded, control device 36 outputs an optical and/or acoustic warning message via data line 59 to an output device 61, where it can be perceived by the operator of sensor arrangement 10.

Figure 5:
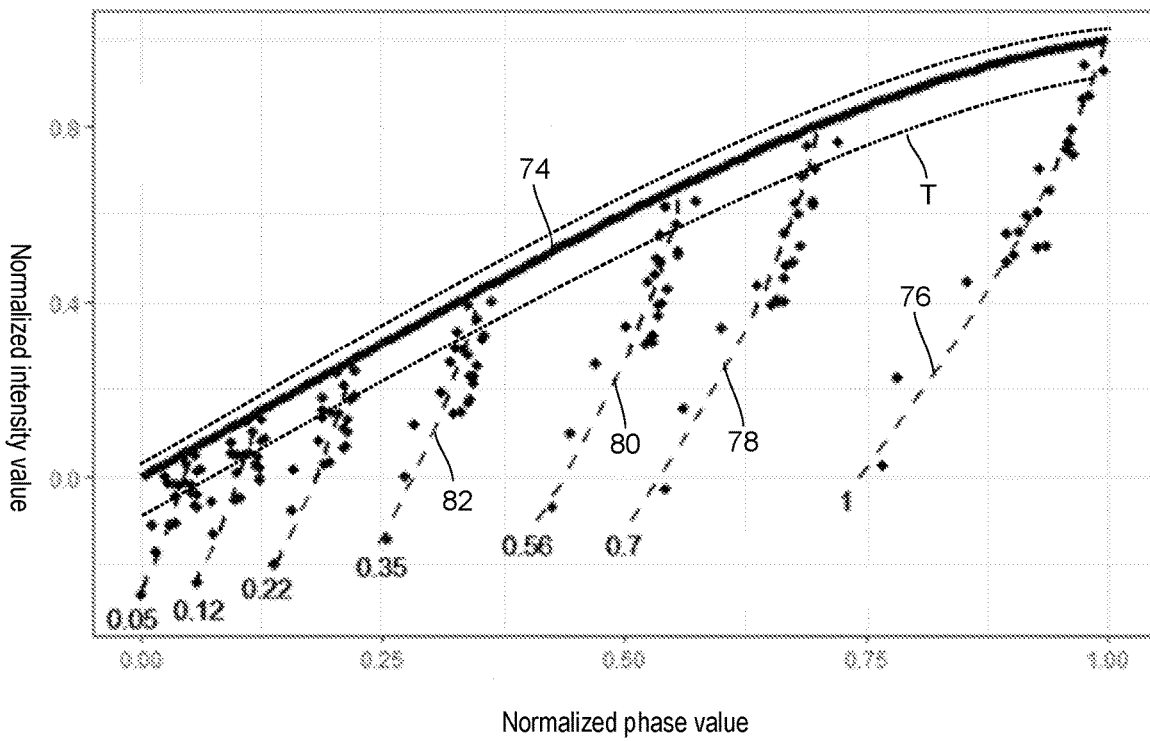
FIG. 5 shows a plot of a normalized dimensionless intensity of a response radiation as a function of a normalized dimensionless phase angle for a freshly calibrated sensor arrangement, having detection-value pairs that were ascertained on differently degraded sensor arrangements.

The response characteristic of Equation 4 is shown in FIG. 5 as graph 74, constituting a reference response characteristic. As long as the response characteristic of sensor arrangement 10 (or of a sensor arrangement of the same type) matches the reference response characteristic at the time of calibration, sensor arrangement 10 supplies value pairs $\phi_{N,j}$, $I_{N,j}$ that lie on graph 74. A calibration value correlation that is based on graph 74, and that links detection values of sensor arrangement 10 with associated result values for the concentration or partial pressure of quencher substance Q in test fluid P, supplies correct result values.

As degradation continues, however, the detection-value pairs $\phi_{N,j}$, $I_{N,j}$ obtained for a test fluid deviate from graph 74. The deviation occurs with increasing degradation along the traces shown in FIG. 5, of which (in the interest of clarity) only the four traces all the way on the right are labeled with reference characters 76 to 82. If the detection-value pairs that are obtained lie outside tolerance band T, control device 36 infers a degradation of the luminophore which is no longer tolerable, and outputs the warning message.

Each of these traces shows the profile of detection-value pairs that are obtained, with increasing degradation, for a test fluid P having a constant concentration of quencher substance Q. The traces shown in FIG. 5 are isoconcentration lines that indicate, in different degradation states, the respective detection-value pairs outputted by sensor arrangement 10 for respectively identical test fluids P having a respectively constant concentration of quencher substance Q. Trace 80 in FIG. 5, for example, indicates the profile of the detection-value pairs that are obtained, proceeding from reference response characteristic 74, for that test fluid which supplies, on the basis of the reference response characteristic, a normalized dimensionless phase value of 0.7. As degradation progresses, even in the normalized dimensionless value space the normalized dimensionless phase values become increasingly lower than when a sensor arrangement that has not yet degraded since the most recent calibration is used.

Isoconcentration lines could also be plotted in the dimension-affected representation of FIG. 4, as shown by trace 68 therein which is likewise an isoconcentration line. The term "isoconcentration line" is thus equivalent in meaning to the term "iso-partial pressure line."

If what is detected in the context of creation of the plot of FIG. 5, using one or several further, freshly calibrated sensor arrangements for each detection point, is the actual concentration (partial pressure) of quencher substance Q in test fluid P, it is then possible to ascertain by means of the above Equation 1, for a known oxygen partial pressure $p_{o_2}$, the hypothetical phase value $\phi_{hyp}$ that would have been ascertained, instead of the phase value actually ascertained with sensor arrangement 10 in different degradation states, if sensor arrangement 10 had been in the calibration state during the respective detection operation.

FIG. 6 is a depiction of the plot of FIG. 5 with a hypothetical detection value, in the form of hypothetical phase value $\phi_{hyp}$, allocated in that manner to each actual detection-value pair. Actually detected detection-value pairs (therefore also called "actual detection-value pairs") are depicted in FIGS. 5 to 7 as solid diamonds. The hypothetical phase value $\phi_{hyp}$ associated with an actual detection-value pair is depicted in FIGS. 5 to 7 as a hollow square.

Depicted in FIG. 6 for five actually detected detection-value pairs, using thin arrows, is the respective deviation of their actually detected phase value from the hypothetical phase value $\phi_{hyp}$ determined based on the known concentration using Equation 1. A hypothetical trace 84 shows the profile of the hypothetical phase values $\phi_{hyp}$ for the actual detection values associated with trace 78.

A mapping instruction, which maps actually detected detection-value pairs at least in terms of one detection value (in the example depicted, the phase value) onto the associated hypothetical detection value, thus furnishes a degradation compensation that converts the detection value needed for identifying the result value from an actual detection value into a hypothetical detection value of a non-degraded sensor arrangement.

One such possible mapping instruction is, for example, Equation 8 below:

$$\psi_N(\phi_N, I_N) = a\phi_N + b\phi_N^2 + cI_N + dI_N\phi_N + eI_N^2 \quad \text{(Eq. 8)}$$

This Equation 8 maps normalized dimensionless detection-value pairs ($\phi_N$, $I_N$) as normalized dimensionless degradation-compensated detection values (in this case, degradation-compensated phase values $\psi_N$). Equation 8 consequently utilizes both the detected intensity and the detected phase value of a detection operation to compensate the phase value in terms of a degradation of the luminophore which has possibly occurred, and consequently to output a model phase value that would have been obtained by sensor arrangement 10 if it had been in the calibrated state during the detection operation. The parameter values that were identified experimentally for the sensor arrangement type of sensor arrangement 10 were a=−1.20, b=−0.2, c=−0.14, d=−0.5, and e=−0.25.

Particularly advantageously, for application of the mapping instruction of Equation 8 it is immaterial whether the luminophore of sensor arrangement 10 is or is not actually degraded. It maps value pairs that satisfy Equation 4 with sufficient accuracy onto itself.

Equation 8 is therefore an example of a compensation value correlation as recited in the introduction to the description. It is stored in data memory 38.

FIG. 7 additionally shows, for actually detected detection-value pairs, the respectively associated degradation-compensated normalized dimensionless phase values using a window symbol.

By replacing the normalized dimensionless phase value $\phi_N$ in Equation 2 with the degradation-compensated phase value $\psi_N$ and by correspondingly readjusting Equation 2, the normalized dimensionless degradation-compensated phase value $\psi_N$ can be converted into a dimension-affected degradation-compensated phase value $\psi$.

If the degradation-compensated phase value $\psi$ is used instead of the phase value $\phi$ in the calibration value correlation of Equation 1, it is possible to identify the desired quencher substance partial pressure correctly therefrom even with a degraded sensor arrangement 10, and to output it via data line 59 to output device 61.

The above value correlations and equations are stored in data memory 38 of control device 36. Control device 36 is embodied to accomplish the above computation operations and thus to calculate a correct result value from a detection value of sensor arrangement 10 even when, because of aging-related degradation of the luminophore, the response characteristic that is the basis of a detection operation differs, in fact differs considerably, from the reference response characteristic that is the basis for the generation of calibration value correlation.

For better comprehension of this complex topic, the procedure for identifying result values from degradation-compensated detection values will be summarized one more time:

Firstly, the Equations 4 and 8 that apply to sensor arrangements of the same design, i.e. for a sensor arrangement type as a whole, are parameterized for the sensor arrangement type by experiments using sensor arrangements of the relevant type in different degradation states and with different test fluids, especially having different concentrations of quencher substance.

The specific sensor arrangement 10 is calibrated, i.e. the parameter values of Equation 1 which are relevant to sensor arrangement 10 are determined based on at least two calibration measurements using test fluids having known concentrations of quencher substance which are quantitatively as different as possible.

Using the calibration, based on the detection values of the calibration measurements and based on Equation 4 along with Equation 5 that has already been parameterized for the sensor arrangement type and converted into Equations 6 and 7, the extreme values $I_{max}$ and $I_{min}$ are determined.

From Equation 1 parameterized by calibration, the extreme values $\phi_{max}$ and $\phi_{min}$ are determined.

Sensor arrangement 10 is then put into productive detection operation. The detected detection values are converted by Equations 2 and 3 into normalized dimensionless detection values.

The normalized dimensionless detection-value pairs ($\phi_N$, $I_N$) are used as arguments in Equation 8. With Equation 8, a normalized dimensionless degradation-compensated detection value is identified for each detection-value pair ($\phi_N$, $I_N$) and is converted, using the correspondingly reconfigured Equation 2, into a dimension-affected degradation-compensated detection value.

Using this dimension-affected degradation-compensated detection value, the result value is identified by way of the parameterized Equation 1 and is outputted by control device 36.

Additionally or alternatively, control device 36 can identify and output the degradation state of the sensor arrangement based on a comparison of the degradation-compensated detection value with the actually detected detection value, whether dimensionless, dimensionless normalized, or dimension-affected, and/or on the basis of a comparison of result values identified on the basis of those two detection values.

Proceeding from this comparison and based on the known degradation curves as depicted in FIGS. 4 to 7, the control device can identify and output an estimate of the remaining lifespan of sensor arrangement 10.

Proceeding from that comparison, the control device can additionally or alternatively output an identified result value based on the actually detected values, for instance when a difference amount between detected values and degradation-compensated detected values is less than or equal to a predetermined acceptance threshold, or can output a result value identified on the basis of the degradation-compensated detected values, for instance when the difference amount between detected values and degradation-compensated detected values is greater than a predetermined acceptance threshold. Preferably outputted along with a result value identified on the basis of the degradation-compensated detected values is a message that that value was not identified directly from the actually detected values.

Control device 36, data memory 38, and output device 61 constitute an evaluation apparatus 63.

The invention claimed is:

1. A method for degradation-compensated evaluation of detection signals of a sensor arrangement operating on the principle of luminescence quenching, which arrangement comprises a luminophore that degrades over time, an excitation radiation source, and at least one optical sensor, the luminophore radiating, in accordance with a response characteristic of the sensor arrangement, in reaction to irradiation with a predefined modulated excitation radiation and as a function of the extent of an interaction of the luminophore with a quencher substance that quenches the luminescence of the luminophore, a response radiation detected by the at least one optical sensor; the sensor arrangement outputting, as detection signals, a detected intensity value representing an intensity of the response radiation and a detected phase value representing a phase difference of the response radiation with respect to the modulation of the excitation radiation; for an accomplished detection of a response radiation, a quantitative deviation of one of the detected values, from among a detected intensity value and detected phase value, being quantitatively decreased in accordance both with the detected intensity value and with the detected phase value, the deviation being based on a degradation-based change in the response characteristic at the time of the accomplished detection, with respect to a reference response characteristic whose basis is a calibration of the sensor arrangement, a degradation-compensated detected value thus being identified; a result value of the accomplished detection, referred to the quencher substance, being determined on the basis of the degradation-compensated detected value in accordance with a predetermined calibration value correlation identified in consideration of the reference response characteristic.

2. The method according to claim 1, further comprising a step of identifying the degradation-compensated detected value on the basis of a predetermined compensation value correlation with input variables on the basis of the detected intensity value and the detected phase value.

3. The method according to claim 1, further comprising a step of transforming both the detected intensity value and the detected phase value, using at least one system parameter characterizing the sensor arrangement and/or at least one process parameter deriving from the detection process, into a dimensionless detected intensity value, and into a dimensionless detected phase value, the predetermined compensation value correlation then being a predetermined dimensionless compensation value correlation in accordance with which, with input variables on the basis of the dimensionless detected intensity value and the dimensionless detected phase value, the dimensionless degradation-compensated detected value is identified.

4. The method according to claim 3, wherein the degradation-compensated detected value is a dimensionless, degradation-compensated detected value; and the predetermined calibration value correlation is a dimensionless, predetermined calibration value correlation, the result value being identified in accordance with the dimensionless calibration value correlation with an input variable on the basis of the dimensionless degradation-compensated value.

5. The method according to claim 1, wherein the degradation-compensated detected value is a degradation-compensated detected phase value.

6. An evaluation apparatus that is embodied to execute the method according to one of the preceding claims and is thus embodied for degradation-compensated evaluation of detection signals of a sensor arrangement that operates according to the principle of luminescence quenching and has a luminophore that degrades over time, has an excitation radiation source, and has at least one optical sensor; the luminophore radiating, in accordance with a response characteristic of the sensor arrangement, in reaction to irradiation with a predefined modulated excitation radiation and as a function of the extent of a contact of the luminophore with a quencher substance that quenches the luminescence of the luminophore, a response radiation detected by the at least one optical sensor; the evaluation apparatus comprising a data input channel that is embodied to transfer from the sensor arrangement to a data processing unit of the evaluation apparatus, as detection signals, the detected intensity value representing the intensity of the response radiation and the detected phase value representing a phase difference of the response radiation with respect to the modulation of the excitation radiation; the data processing unit comprising a data memory for storing data and a computation unit for processing data; at least the predetermined calibration value correlation identified in consideration of the reference response characteristic being stored in the data memory; the evaluation apparatus being embodied to ascertain the degradation-compensated detected value from the detected intensity value and detected phase value in accordance with both the detected intensity value and the detected phase value, and to determine and output the result value, referred to the quencher substance, of the accomplished detection in accordance with the calibration value correlation on the basis of the degradation-compensated detected value.

7. The evaluation apparatus according to claim 6, wherein the predetermined compensation value correlation is also stored in the data memory, the computation unit being embodied to identify the degradation-compensated detected value in accordance with the predetermined compensation value correlation with input values on the basis of the detected intensity value and of the detected phase value.

8. The evaluation apparatus according to claim 6, wherein the evaluation apparatus is embodied to transform both the detected intensity value and the detected phase value, utilizing at least one system parameter characterizing the sensor arrangement and/or at least one process parameter deriving from the detection process, into a dimensionless detected intensity value, and into a dimensionless detected phase value; the predetermined compensation value correlation being a predetermined dimensionless compensation value correlation in accordance with which, with input variables on the basis of the dimensionless detected intensity value and the dimensionless detected phase value, the dimensionless, degradation-compensated detected value is identified.

9. The evaluation apparatus according to claim 8, wherein the degradation-compensated detected value is a dimensionless, degradation-compensated detected value; and the predetermined calibration value correlation is a dimensionless, predetermined calibration value correlation, the evaluation apparatus being embodied to ascertain the result value in accordance with the dimensionless calibration value correlation with an input variable on the basis of the dimensionless degradation-compensated value.

10. The evaluation apparatus according to claim 6, wherein the degradation-compensated detected value is a degradation-compensated detected phase value.

11. A measurement arrangement encompassing an evaluation apparatus according to claim 6 and a sensor arrangement having a luminophore that degrades over time, having an excitation radiation source, and having at least one optical sensor; the luminophore radiating, in accordance with a response characteristic of the sensor arrangement, in reaction to irradiation with a predefined modulated excitation radiation and as a function of the extent of a contact of the luminophore with a quencher substance that quenches the luminescence of the luminophore, a response radiation detected by the at least one optical sensor.

12. The method according to claim 1, further comprising a step of transforming both the detected intensity value and the detected phase value, using at least one system parameter characterizing the sensor arrangement and/or at least one process parameter deriving from the detection process, into a dimensionless normalized detected intensity value, and into a dimensionless normalized detected phase value, the predetermined compensation value correlation then being a predetermined dimensionless compensation value correlation in accordance with which, with input variables on the basis of the dimensionless detected intensity value and the dimensionless detected phase value, the dimensionless normalized, degradation-compensated detected value is identified.

13. The method according to claim 3, wherein the degradation-compensated detected value is a dimensionless normalized, degradation-compensated detected value; and the predetermined calibration value correlation is a dimensionless normalized, predetermined calibration value correlation, the result value being identified in accordance with the dimensionless calibration value correlation with an input variable on the basis of the dimensionless degradation-compensated value.

14. The evaluation apparatus according to claim 6, wherein the evaluation apparatus is embodied to transform both the detected intensity value and the detected phase value, utilizing at least one system parameter characterizing the sensor arrangement and/or at least one process parameter deriving from the detection process, into a dimensionless normalized detected intensity value, and into a dimensionless normalized detected phase value; the predetermined compensation value correlation being a predetermined dimensionless compensation value correlation in accordance with which, with input variables on the basis of the dimensionless detected intensity value and the dimensionless detected phase value, the dimensionless normalized, degradation-compensated detected value is identified.

15. The evaluation apparatus according to claim 8, wherein the degradation-compensated detected value is a dimensionless normalized, degradation-compensated detected value; and the predetermined calibration value correlation is a dimensionless normalized, predetermined calibration value correlation, the evaluation apparatus being embodied to ascertain the result value in accordance with the dimensionless calibration value correlation with an input variable on the basis of the dimensionless degradation-compensated value.

* * * * *